US00PP35476P2

(12) United States Plant Patent
Van Swieten

(10) Patent No.: US PP35,476 P2
(45) Date of Patent: Nov. 14, 2023

(54) ***PHALAENOPSIS* ORCHID PLANT NAMED 'PHA632612'**

(50) Latin Name: ***Phalaenopsis* hybrid**
Varietal Denomination: PHA632612

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/803,999

(22) Filed: Feb. 24, 2023

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — Jondle & Associates, P.C.

(57) ABSTRACT

A new and distinct variety of *Phalaenopsis* plant named 'PHA632612', particularly characterized by having numerous attractive, light reddish-purple flowers with dark purplish-red flecks and reddish-purple lips; flowers that are flat in lateral view, and lips having medium curvature of the lateral lobe, is disclosed.

3 Drawing Sheets

Genus and species: *Phalaenopsis* hybrid.
Variety denomination: 'PHA632612'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA632612'.

The new *Phalaenopsis* plant is a product of a planned breeding program conducted by the inventor in Bleiswijk, the Netherlands. The objective of this breeding program was to create a new *Phalaenopsis* plant with numerous attractive light reddish-purple flowers with dark purplish-red lips suitable for potted plant production.

The new *Phalaenopsis* plant 'PHA632612' is a result of cross-pollination made by the inventor in June 2013 in Bleiswijk, the Netherlands, of the proprietary female, or seed parent, *Phalaenopsis* hybrid '07-006240-0002' (unpatented), with a proprietary male, or pollen parent, *Phalaenopsis* hybrid 'PHALFNIWIN' (U.S. Plant Pat. No. 29,629).

The new *Phalaenopsis* was selected by the inventor as a single plant within the progeny of the stated cross-pollination in a controlled greenhouse in Bleiswijk, the Netherlands, in May 2016. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 22, 2021 (Application No. 2021/1098), by Applicant who obtained the subject matter disclosed directly from the inventor. 'PHA632612' has not been made publicly available or sold anywhere in the world prior to the effective filing date of this application with the exception of sales or disclosures made one year or less before the effective filing date of this claimed invention by Applicant who obtained 'PHA632612' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA632612' as a new and distinct variety of *Phalaenopsis* plant:

1) Light reddish-purple flowers with dark purplish-red flecks and reddish-purple lips (number and intensity of flecks depend on the temperature during growing period);
2) Flower shape in lateral view is flat; and
3) Lips, curvature of lateral lobes is medium.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in September 2022. Colors in the photographs may differ from the color values cited in the detailed botanical description, which accurately describe the actual colors of the new variety.

DESCRIPTION OF THE NEW VARIETY

Figure 1:
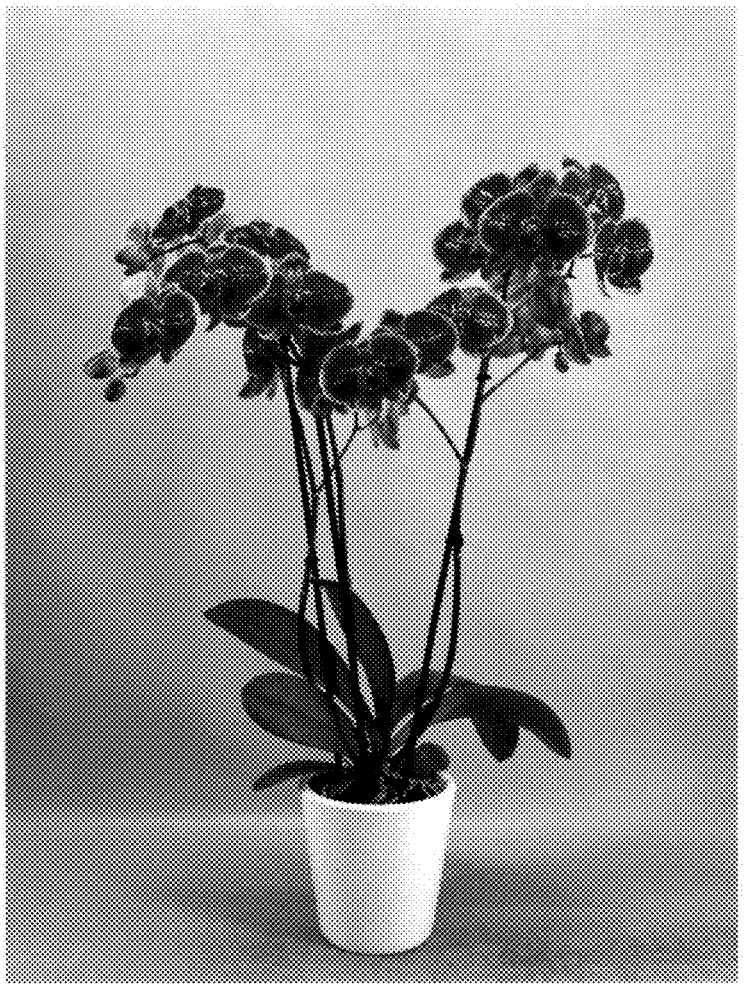
FIG. 1 shows the overall plant habit, including blooms, buds, and foliage of 'PHA632612'.
Figure 2:
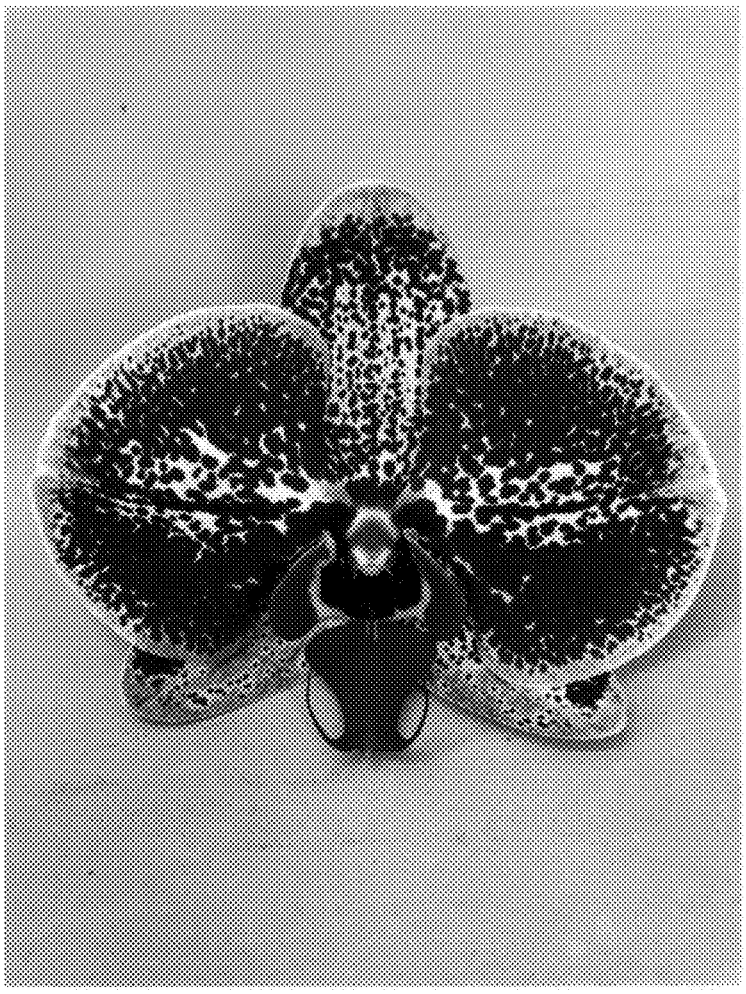
FIG. 2 shows a close-up of a flower of 'PHA632612'.
Figure 3:
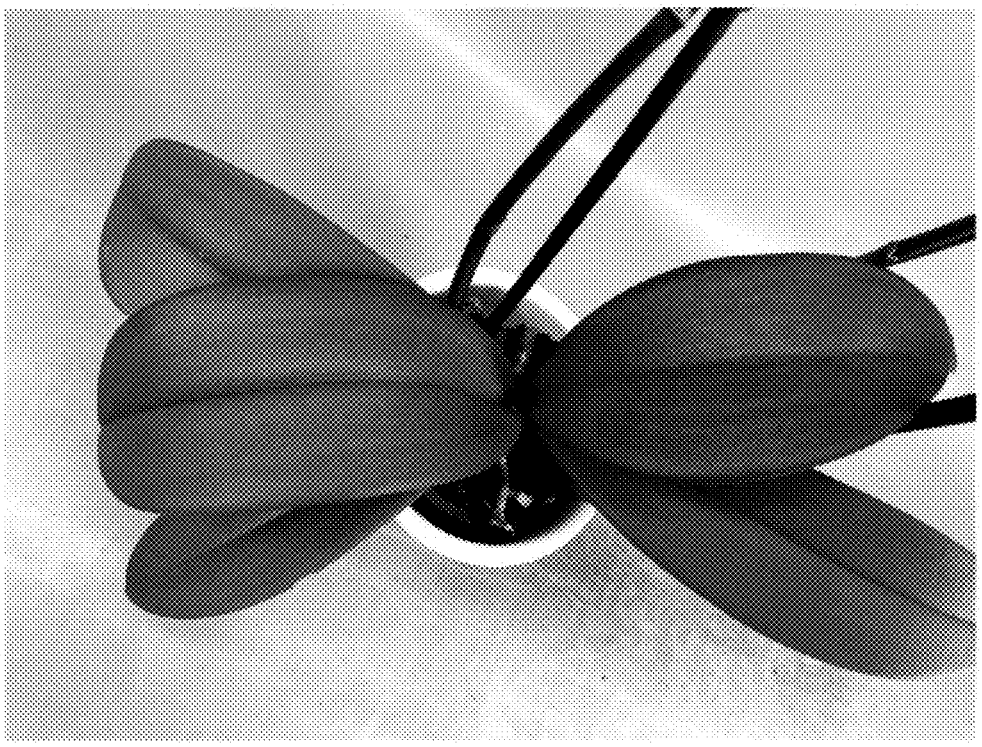
FIG. 3 shows a close-up, overhead view of the leaves of 'PHA632612'.

The following detailed description sets forth the distinctive characteristics of 'PHA632612'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in September 2022 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'*PHA*632612'.

Parentage:

*Female parent*.—*Phalaenopsis* cultivar '07-006240-0002' (unpatented).

*Male parent*.—*Phalaenopsis* cultivar 'PHALFNIWIN' (unpatented).

Propagation:

*Type*.—Meristem tissue culture.

Roots:

*Root description*.—Greyed-green (a color in between RHS 190B and RHS 190C) colored roots with branching lateral roots having purplish-red (RHS N77B) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle and raceme inflorescence.

*Height* (*from soil level to top of inflorescence*).—Approximately 57.0 cm to 62.0 cm.

*Width* (*measured from leaf tips*).—About 38.0 cm to 40.0 cm.

*Vigor*.—Strong.

Leaves:

*Mature leaves*.—Quantity per plant: 8 to 10 leaves are produced before flowering. Length (fully expanded): 20.0 cm to 22.0 cm. Width: 7.5 cm to 8.5 cm. Position of the broadest part of the leaf: At the middle. Shape: Oblong. Base shape: Moderately elongated. Apex: Obtuse asymmetric. Leaf blade angle with the petiole (measured from the horizontal position): Between 25 degrees and 40 degrees. Leaf margin: Entire. Color: Upper surface: RHS 146A with a brown (RHS 200C) margin toward the tips. Lower surface: RHS 144A with a reddish-brown (RHS 200B) margin toward the tips. Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: RHS 144A.

Peduncle:

*Quantity per plant*.—1 to 3.

*Number of flowers per peduncle*.—12 to 17.

*Length*.—57.0 cm to 62.0 cm.

*Diameter*.—5.0 mm to 6.0 mm.

*Strength*.—Strong.

*Aspect*.—Upright to slightly pendent.

*Texture*.—Smooth.

*Color*.—Mix of brown (RHS 200B) and green (RHS 146B).

*Internode length*.—3.5 cm to 4.5 cm.

Inflorescence description:

*Appearance*.—Upright to slightly pendent, panicle and raceme inflorescence with bilaterally symmetrical flowers that open in succession beginning with the lowermost flower.

*Number of inflorescences*.—1 to 3.

*Inflorescence size*.—Height (from base to tip): 240.0 mm to 340.0 mm.

*Flowering time*.—First flowers can be expected 10 to 11 months after planting in a 12-cm pot.

*Flower*.—Height: 75.0 mm to 80.0 mm. Diameter: 90.0 mm to 95.0 mm. Depth of lip: 24.0 mm to 26.0 mm.

*Flower shape*.—Flat.

*Flower longevity*.—On the plant: 10 to 12 weeks.

*Fragrance*.—Absent.

*Flower bud*.—Average size: Large. Length: 23.0 mm to 25.0 mm. Width: 19.0 mm to 21.0 mm. Shape: Egg shaped. Color: Yellow-green (RHS 145C) with purplish-red (RHS N77B) shade and stripes.

*Petals*.—Arrangement: Open/free. Shape: Semi-circular. Apex: Emarginated asymmetric. Margin: Entire. Length (from base to tip): 42.0 mm to 44.0 mm. Width: 50.0 mm to 52.0 mm. Position of the broadest part of the petal: Toward the base. Color (when fully opened): Upper surface: Basic color: Light reddish-purple (RHS N78D). Over color: Dark purplish-red (RHS N79C) flecks. Lower surface: Basic color: Very light purple (RHS 76B). Over color: Diluting reddish-purple (RHS N77C) flecks. Number of spots and stripes on the petals (upper surface): Many to very many flecks. Color of spots and stripes on the petals (upper surface): RHS N79C. Density of netting of the petals (upper surface): None. Color of the netting (upper surface): Not applicable.

*Dorsal sepal*.—Shape: Elliptic. Apex: Slightly emarginated symmetric. Margin: Entire. Length (from base to tip): 42.0 mm to 44.0 mm. Width: 36.0 mm to 38.0 mm. Position of the broadest part of the dorsal sepal: At middle. Color (when fully opened): Upper surface: Basic color: Light reddish-purple (RHS N78D). Over color: Dark purplish-red (RHS N79C) flecks and purplish-pink (RHS N78C) netting. Lower surface:. Basic color: Light purple (RHS 76A). Over color: Purplish-pink (RHS N78C) shade and diluting reddish-purple (RHS N77C) flecks.

Number of spots and stripes on the dorsal sepal (upper surface): Many to very many flecks. Color of spots and stripes on the dorsal sepal (upper surface): RHS N79C. Density of netting of the dorsal sepal (upper surface): Very low. Color of the netting (upper surface): RHS N78C.

*Lateral sepals*.—Shape: Ovate. Apex: Obtuse asymmetric. Margin: Entire. Length (from base to tip): 44.0 mm to 46.0 mm. Width: 25.0 mm to 27.0 mm. Position of the broadest part of the lateral sepals: Toward the base. Color (when fully opened): Upper surface: Basic color: Very light pink (RHS 76C). Over color: Purplish-pink (RHS N78C) shade; dark purplish-red (RHS N79C) flecks. Lower surface: Basic color: Very light purple (RHS 76B). Over color: Reddish-purple (RHS N78B) shade; diluting reddish-purple (RHS N77C) flecks. Number of spots and stripes on the lateral sepals (upper surface): Many flecks. Color of spots and stripes on the lateral sepals (upper surface): Flecks RHS N79C. Density of netting of the lateral sepals (upper surface): None. Color of the netting (upper surface): Not applicable.

*Labellum* (*lip*).—Whiskers: Present. Length of whiskers: 16.0 mm to 18.0 mm. Color of whiskers: Purple-red (color in between RHS N78A and RHS N79C); yellow (RHS 7B) tips. Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Slightly undulated. Length: 19.0 mm to 21.0 mm. Width: 13.0 mm to 15.0 mm. Color: Upper surface: White (RHS NN155C) with touch of yellow (RHS 7A) and dark red (RHS 187A) fleck at the base; red (RHS 185A) on one side and reddish-purple (RHS N78A) with a few strips toward the tip. Lower surface: White (RHS NN155C) at the base with a touch of yellow (RHS 7B); red (RHS 185A) on one side and reddish-purple (RHS N78B) toward the tip. Number of spots and stripes on the lateral lobe: One fleck and few stripes. Color of spots and stripes on the lateral lobe: Fleck RHS 187A and stripes RHS N78A. Density of netting of the lateral lobe: None. Color of the netting: Not applicable.

*Apical lobe*.—Shape: Triangular. Margin: Entire. Length: 19.0 mm to 21.0 mm. Width: 18.0 mm to 20.0 mm. Color: Upper surface: Yellow (RHS 7A) and red (RHS 185A) margin at the base; dark purplish-red (color in between RHS N79C and RHS N78A) toward whiskers. Lower surface: Dark reddish-orange (RHS 178B) at the base; reddish-purple (RHS N78A) at the middle from base and along margin toward whiskers; very light purple (RHS 78B) at the middle toward tip. Number of spots and stripes on the apical lobe: None. Color of spots and stripes on the apical lobe: None. Density of netting of the apical lobe: None. Color of the netting: None. Bump and ridge (upper and lower surface): Absent.

*Callus*.—Average size: Large. Height: 8.0 mm to 9.0 mm. Length: 7.0 mm to 8.0 mm. Width: 5.0 mm to 6.0 mm. Color: Greenish-yellow (RHS 6C) at the base; yellowish-green (RHS 155A) on sides and dark red (RHS 187A and RHS 200A) flecks.

Reproductive organs:

*Column*.—Length: 8.0 mm to 9.0 mm. Diameter: 5.0 mm to 6.0 mm. Color: White (RHS NN155C) at the base; reddish-purple (RHS N78B) toward the tips.

*Pollinia*.—Quantity: 2. Diameter: 0.9 mm to 1.0 mm. Color: Orange-yellow (RHS 23A).

*Ovary*.—Length: 13.0 mm to 15.0 mm. Diameter: 2.0 mm to 2.3 mm.

*Pedicel*.—Length: 36.0 mm to 38.0 mm. Diameter: 2.4 mm to 2.8 mm. Color: Yellow-green (RHS 146B) at the base; light yellow-green (RHS 145C) with a touch of very light purple (RHS 76B) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA632612' differs from the female parent plant, cultivar '07-006240-0002' (unpatented), in that 'PHA632612' has flowers and callus having a flecked pattern, whereas '07-006240-0002' has flowers having a striped pattern and callus having a dotted pattern. Additionally, 'PHA632612' has flowers that are light reddish-purple, whereas '07-006240-0002' has reddish-purple flowers.

'PHA632612' differs from the male parent plant, cultivar 'PHALFNIWIN' (U.S. Plant Pat. No. 29,629), in that 'PHA632612' has a moderately compressed semi-circular petal shape, flat flower shape in lateral view, and longer leaves, whereas 'PHALFNIWIN' has petals that are moderately compressed, convex flower shape in the lateral view, and shorter leaves.

'PHA632612' is most similar to the commercial *Phalaenopsis* plants named 'PHALGULFQ' (U.S. Plant Pat. No. 29,975) and 'PHALFOYX' (U.S. Plant Pat. No. 28,103). 'PHA632612' differs from the commercial variety 'PHALGULFQ' in that 'PHA632612' has light reddish-purple flowers having a flecked pattern, whereas 'PHALGULFQ' has white flowers that are flecked, edged, and shaded. Additionally, 'PHA632612' has longer whiskers that are purple-red with yellow tips, whereas 'PHALGULFQ' has shorter whiskers that are very light purple.

'PHA632612' differs from the commercial variety 'PHALFOYX' in that 'PHA632612' has light reddish-purple flowers having a flecked pattern, whereas 'PHALFOYX' has white flowers that are dotted, flecked, and edged. Additionally, 'PHA632612' has longer whiskers that are purple-red with yellow tips, whereas 'PHALFOYX' has shorter whiskers that are dark red with light greenish-yellow tips.

I claim:

1. A new and distinct variety of *Phalaenopsis* plant named 'PHA632612', substantially as described and illustrated herein.

* * * * *